(12) United States Patent
White et al.

(10) Patent No.: US 9,138,520 B2
(45) Date of Patent: *Sep. 22, 2015

(54) TOTAL CHLORINE WATER DETECTION SYSTEM AND METHOD FOR MEDICAL FLUID TREATMENTS

(71) Applicants: Baxter International Inc., Deerfield, IL (US); Baxter Healthcare S.A., Glattpark (Opfikon) (CH)

(72) Inventors: Jeff White, Waukegan, IL (US); Ye Chen, Buffalo Grove, IL (US); Samuel Ding, Libertyville, IL (US); Joel Titus, Lake Zurich, IL (US); Justin Rohde, Des Plaines, IL (US); Shincy Maliekkal, Glenview, IL (US); Kevin Cooper, Libertyville, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 116 days.

This patent is subject to a terminal disclaimer.

(21) Appl. No.: 13/797,066

(22) Filed: Mar. 12, 2013

(65) Prior Publication Data

US 2014/0110340 A1     Apr. 24, 2014

Related U.S. Application Data

(60) Provisional application No. 61/716,966, filed on Oct. 22, 2012.

(51) Int. Cl.
*A61K 33/14*     (2006.01)
*A61M 1/14*      (2006.01)
(Continued)

(52) U.S. Cl.
CPC ............... *A61M 1/14* (2013.01); *A61M 1/1656* (2013.01); *G01N 27/4168* (2013.01); *Y10T 436/193333* (2015.01)

(58) Field of Classification Search
CPC ...... A61K 33/14; A61M 1/0209; A61M 1/16; A61M 1/656; A61M 1/3462; A61M 1/3643; A61M 2001/165; A61M 2001/1609; A61M 2001/1666; A61M 2001/3437; B01D 35/143; B01D 61/08; B01D 61/12; C02F 1/003; C02F 1/008; C02F 1/283; C02F 1/325; C02F 1/441
USPC ........ 210/85, 96.2, 252, 646, 647; 422/82.05, 422/82.09
See application file for complete search history.

(56) References Cited

U.S. PATENT DOCUMENTS 2,585,059 A *   2/1952   Wallace ........................ 204/400
3,966,413 A     6/1976   Marinenko (Continued)

FOREIGN PATENT DOCUMENTS

EP     1304559       4/2003
WO     WO96/25214    8/1996

OTHER PUBLICATIONS

Manns et al., The acu-menTM: A new device for continuous renal replacement therapy in actue renal failure, Kidney International, 1998, pp. 268-274, vol. 54.

(Continued)

*Primary Examiner* — Bobby Ramdhanie
*Assistant Examiner* — Hayden Brewster
(74) *Attorney, Agent, or Firm* — K&L Gates LLP

(57) ABSTRACT

A system and method for determining a concentration of total chlorine in dialysis water are provided. The system comprises a main unit housing a KI/water sample chamber and a sodium sulfate chamber. A first electrode pair bridges the two chambers and generates tri-iodide proportional to the amount of total chlorine in the water sample. A second electrode pair in contact with fluid in the KI/water sample detects an amount of tri-iodide generated by the first electrode pair. The system is suitable for use in connection with, or for incorporation into, a water purification system for generating dialysis fluid, and may include a display that alerts the user to stop or prevent a hemodialysis treatment if the total chlorine level exceeds a predetermined level.

19 Claims, 9 Drawing Sheets

(51) Int. Cl.
    *A61M 1/16* (2006.01)
    *G01N 27/416* (2006.01)
    *C02F 3/28* (2006.01)

(56) References Cited

U.S. PATENT DOCUMENTS

| | | | |
|---|---|---|---|
| 4,049,382 A | | 9/1977 | Ross et al. |
| 5,346,605 A | * | 9/1994 | Wolcott et al. ............... 204/412 |
| 7,985,377 B2 | * | 7/2011 | Vincent ..................... 422/82.01 |
| 2010/0051552 A1 | * | 3/2010 | Rohde et al. ................. 210/647 |
| 2012/0103823 A1 | * | 5/2012 | Dweik et al. ................. 205/335 |

OTHER PUBLICATIONS

Saad et al., "Sequential Flow Injection Determination of Chlorine Species Using a Triiodide-selective Electrode Detector," Analytical Sciences, Vo. 22, Jan. 2006, pp. 45-50.
Oliveira et al., "A coulometric flow cell for in-line generation of reagent, titrant or standard solutions," Microchemical Journal, vol. 82, 2006, pp. 220-225.
Marks, et al., "Amperometric Methods in Control of Water Chlorination," Analytical Chemistry, vol. 19, No. 3, 1947, pp. 200-204.
Nascimento, et al., "Automatic determination of chlorine without standard solutions using a biamperometric flow-batch analysis system," Talanta, vol. 81, No. 1, 2010, pp. 609-613.
Ijspeerd, et al., "Biamperometric determination of free chlorine, hypochlorite, chlorite and chlorate in sodium chloride brine," Fresenius' Zeitschrift für analytische Chemie, vol. 288, No. 5, 1977, pp. 357-360.
Lichtig, et al., "Biamperometry in the Diffusion Current Region: Considerations for Its Application in Trace Analysis," Biamperometry & Trace Analysis, vol. 4, No. 3, 1993, pp. 172-178.
Rigdon, et al., "Determination of residual chlorine in water with computer automation and residual-chlorine electrode," Analytical Chemistry, vol. 50, No. 3, 1978, pp. 465-469.
Len, et al., "Effects of storage conditions and pH on chlorine loss in electrolyzed oxidizing (EO) water," Journal of Agricultural and Food Chemistry, vol. 50, No. 1, 2002, pp. 209-212.

Hahn, et al., "Electrochemical investigation of chloramine T," Analytica chimica acta, vol. 289, No. 1, 1994, pp. 35-42.
TVA EPA Microprocessor-Controlled Ion Selective Electrode Determination of Total Chlorine by Lymna H. Howe, Reginald E. Hadley and Gary A. Fischer, Office of Natural Resources, Interagency Energy/Environment R&D Program Report, Mar. 1982, 202 pages.
Orion Residual Chlorine Electrode instruction manual, 2003, 35 pages.
Dimmock, et al., "Performance of the Orion 97-70 total residual chlorine electrode at low concentrations and its application to the analysis of cooling waters," Talanta, vol. 29, No. 7, 1982, pp. 557-567.
Seymour, et al., "Reaction with N, N-Diethyl-p-phenylenediamine: A Procedure for the Sensitive Square-Wave Voltammetric Detection of Chlorine," Electroanalysis, vol. 15, No. 8, 2003, pp. 689-694.
Gottardi, et al., "Redox-iodometry: a new potentiometric method," Analytical and Bioanalytical Chemistry, vol. 382, No. 5, 2005, pp. 1328-1338.
Ohura, et al. "Simultaneous potentiometric determination of ClO3—ClO2-and ClO3—HClO by flow injection analysis using Fe (III)-Fe (II) potential buffer," Talanta, vol. 49, No. 5, 1999, pp. 1003-1015.
Whitney, et al., "Solubility of chlorine in water," Industrial & Engineering Chemistry, vol. 33, No. 6, 1941, pp. 741-744.
Li, et al., "The determination of iodide based on a flow-injection coupling irreversible biamperometry," Chinese Chemical Letters, vol. 16, No. 12, 2005, pp. 1629-1632.
Tougas,et al., "Theoretical and experimental response of a biamperometric detector for flow injection analysis," Analytical Chemistry, vol. 57, No. 7, 1985, pp. 1377-1381.
International Search Report for International Application No. PCT/US2013/065953 mailed on Jan. 31, 2014.
Written Opinion for International Application No. PCT/US2013/065953 mailed on Jan. 31, 2014.
W. Gottardi, et al., "Redox-iodometry: a new potentiometric method," Analytical and Bioanalytical Chemistry, vol. 382, No. 5, Jun. 25, 2005, pp. 1328-1338, XP055098367.

* cited by examiner

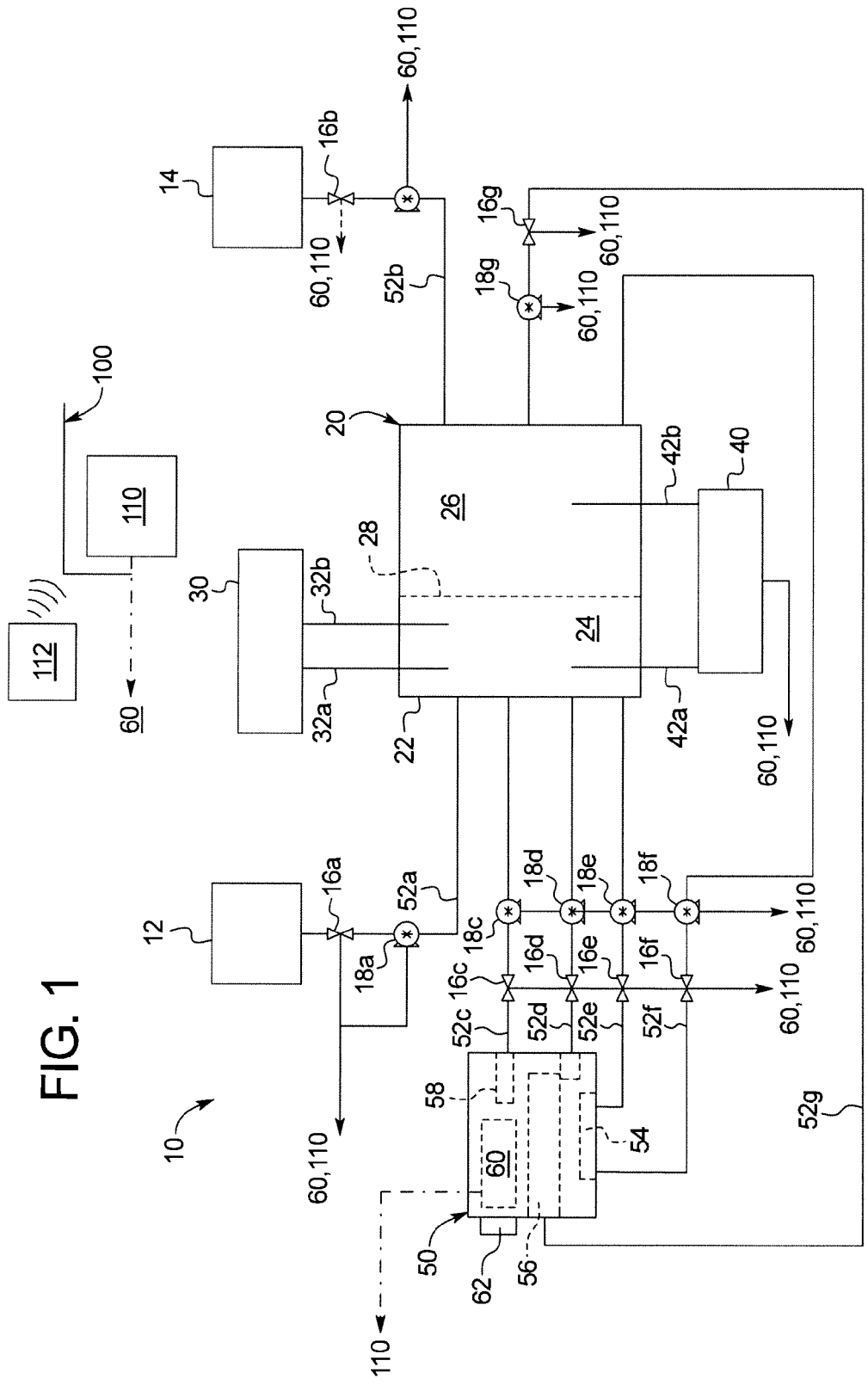

TOTAL CHLORINE WATER DETECTION SYSTEM AND METHOD FOR MEDICAL FLUID TREATMENTS

PRIORITY CLAIM

This application claims priority to U.S. provisional patent application Ser. No. 61/716,966, filed on Oct. 22, 2012, the entire contents of which are incorporated herein by reference and relied upon.

CROSS-REFERENCE TO RELATED APPLICATIONS

This application is being filed concurrently with, and includes related subject matter to, U.S. patent Publication Ser. No. 13/797,086, entitled "Integrated Water Testing System And Method For Ultra-Low Total Chlorine Detection", which claims priority to U.S. provisional patent application Ser. No. 61/716,970, filed on Oct. 22, 2012, the entire contents of which are incorporated herein by reference and relied upon.

BACKGROUND

This application relates generally to water purity qualitative analysis, and in particular to water used for medical applications.

Water purity qualitative analysis determines the presence or absence and the amounts of chemicals and their mixtures in water. Water purity qualitative analysis can require field kits for testing the water facilities. The field test kits are known in general to have disadvantages including inaccuracies in data, false positives, limitations of single-factor testing, e.g., in measuring chlorine levels in pools and spas, and overall accuracy. Disadvantages of field qualitative testing kits also include an inability to reproduce statistics. Outdoor and indoor conditions, such as humidity, temperature, wind, rain and noise add to the inherent disadvantages of test kit qualitative field-type water monitoring.

Testing can alternatively be done by mixing water with powders in vials. Both strips and vials change the color of water to indicate if the water purity meets safe levels. Color change analysis leaves open the possibility that the person viewing the change cannot see color well and that multiple viewers may compare the water color to the test markers differently. Color viewing test results accordingly provide low to moderate accuracy in measuring amounts of chlorine, bacteria and acidity (pH levels), which each affect water purity.

Sensors are used in municipal, industrial and residential water systems to test variables affecting water purity for human consumption and use, as well as to monitor water purity for healthy ecosystems of other living organisms. Sensors measure temperature, pH levels and desalination (salt control) compounds. However, using sensors in qualitative water purity field testing can result in drawbacks due to moderate measurement accuracy for multiple types of water purity statistics.

Using chemistry-based field-testing to gather qualitative water-purity data gives incomplete statistical outcomes, similar to the pH colorimetric qualitative testing. Operating at a neutral pH, chemistry-based testing, like colorimetric testing, measures particular aspects of inorganic substances in water, rather than all its characteristics. As an example, at neutral pH, both of the chemistry-based and colorimetric tests measure dissolved iron amounts, but not iron particles. In addition, ammonia levels from biological decay compromise qualitative measurements using chemistry-based field testing of nutrients in wastewater.

As discussed above, known water testing techniques have multiple drawbacks. In a medical setting in which the testing techniques are relied upon, for example before allowing a therapy to take place, the ramifications associated with inaccurate testing can be serious. If the water testing underreports the level of a certain substance in the tested water, the water can be allowed to be used when it should not be, resulting in a potentially unsafe condition for the patient or in the malfunctioning of a machine running a medical treatment for the patient. The reverse situation is also problematic. If the testing is oversensitive, or in any case gives false positive or over-reported results, the system may needlessly alarm or erroneously prevent a treatment from occurring.

Another problem with the above testing is its manual nature. Even if the testing assay is otherwise sound, the patient or caregiver can introduce error. And even if the testing and the operator performance are sound, manual testing still requires extra steps, adding time, complexity and cost.

An improved water quality system and method are needed accordingly.

SUMMARY

The present disclosure relates to water testing and in particular to the testing of total chlorine in water. One application for the testing system and methodology of the present disclosure is to make water for use with online hemodialysis. Online hemodialysis makes dialysate from purified water. The purified water can be made from house tap water. In a hospital or clinic, the house tap water is the water found for example at sinks and drinking fountains in the hospital or clinic. At home, the tap water is the patient's home tap water.

Making dialysate from purified tap water involves adding salts to the purified water. The goal is to achieve the electrolyte status of blood plasma, or the water component of blood. Because hemodialysis works on the principles of osmosis, diffusion and/or equilibration, the treatment needs to use a treatment fluid, or dialysate, that has the chemical composition of purified blood. There are many components to the patient's blood that are healthy and needed and should not be removed during treatment. Red and white blood cells and platelets are examples. But these healthy and needed components are retained mechanically by making the pores in the dialyzer membranes too small for the cells and the platelets to pass through from the patient or blood side of the dialyzer to the treatment or dialysate side of the dialyzer.

Salts or electrolytes such as a potassium, calcium, sodium and magnesium are also, at least to a certain extent, healthy and needed components of blood. But salts are dissolved in the blood water or plasma. Thus if pure water were to be run as treatment fluid instead of dialysate, the large osmotic or diffusive gradient would pull too much of the salt from the blood and create a highly unsafe condition for the patient. For that reason, great care is taken in the online manufacture of dialysate from purified water to ensure that a desired amount of salt is present in the dialysate before the dialysate is allowed to be delivered to the dialyzer and osmotically or diffusively comingle with the patient's blood.

One method for ensuring that a desired amount of salt is present in the dialysate is through the use of conductivity sensors. Adding salt to the purified water generator increases electrical conductivity sensed by the sensors. The desired amount of salt will have a specific conductivity. The online machine mixes pure water and salts from concentrate containers until the desired conductivity is sensed, after which the dialysate can be delivered to the dialyzer.

The online hemodialysis system contemplated for use with the present system and methodology employs a water purification system that removes preexisting salts (e.g., ions), such as chlorine, from the incoming tap water so that the dialysate generation portion of the system can begin with salt-less, zero-conductivity water to which desired, blood-friendly salts are added. Also, free chlorine in dialysate can cross the dialysis membrane and destroy the patient's red blood cells. Free chlorine in solution can also generate chloramines, which are known to induce hemolytic anemia. The useful lifetime of dialysis membranes is also shortened when free chlorine is present in dialysate. For at least these reasons, AAMI/ANSI recommends that dialysate contain less than 0.5 mg/L of free chlorine.

The present system and method provides a way to automatically and precisely detect either (i) the incoming total chlorine level of the tap water or (ii) the total chlorine level present after the tap water has flowed through a filter intended to remove impurities such as active chlorine compounds (e.g., a filter check). The system and method do not require input from the patient or caregiver. The system and method are also accurate, so that the system alarms or otherwise responds when chlorine levels are too high but greatly reduces the amount of false trips and needless treatment shutdowns.

In an embodiment, the system and corresponding method include a main testing unit in fluid communication with an iodide reservoir and a reducing agent reservoir. A membrane is provided with and divides the main unit into a reducing agent chamber and an iodide and water sample chamber, which are in fluid communication with the reducing agent reservoir and the iodide reservoir, respectively. The main unit further includes two electrode pairs. A tri-iodide generation loop circuit includes the two probes or electrodes of the first pair and bridges the membrane such that a first probe resides in the reducing agent chamber and a second probe resides in the iodide and water sample chamber. A second, tri-iodide detection circuit includes two probes, or electrodes both of which are placed in the iodide and water sample chamber. In some embodiments, the iodide and water sample chamber is a tube disposed within the reducing agent chamber, which may also be a tube. In some embodiments, the iodide and water sample chamber is in fluid communication with the reducing agent chamber via microchannels, for example in a cassette.

In an embodiment, water quality is tested by determining a level of total chlorine. In such an embodiment, a water sample is provided to the iodide and sample chamber of the main testing unit. Once the water sample is pumped to the iodide and sample chamber, a baseline voltage is measured and converted into a baseline current measurement. Then, a voltage is applied to the two electrodes of the tri-iodide generation loop circuitry. The voltage produces tri-iodide from the iodide source (e.g., KI and/or NaI). This production of tri-iodide causes current to flow through the electrodes of a detection circuit. The electrodes of the detection circuitry signal the amount of tri-iodide generated to a computer or control unit by measuring voltage across a resistor produced when the current flows through the generation circuitry. The voltage measurement that takes place in the presence of total chlorine can also be replicated by applying current to the system to generate tri-iodide artificially. Because the amount of tri-iodide generated in this artificial manner can be known by measuring the amount of current applied, it provides for an effective calibration of the measurement system, thereby enhancing accuracy.

In an embodiment, the concentration of total chlorine in water under test is determined by first measuring an initial, background voltage associated with any tri-iodide that may already be in the system (e.g., without generating any tri-iodide or adding external tri-iodide). In one embodiment, the background voltage or current (calculated using Ohm's law) is subtracted from subsequent voltage or current measurements. The sample of water for testing is then added to the test chamber and a baseline voltage measurement is taken, which can then optionally be converted into a baseline current reading using Ohm's law. This step is followed by repeated cycles of (a) generating tri-iodide by application of current to the generation circuit and (b) measuring the resulting voltage in the detection circuit. The plurality of voltage measurements (or current measurements calculated from the plurality of voltage measurements) are plotted against relative or absolute tri-iodide concentration. In this way, a calibration curve including a baseline, the test measurement, and several additional data points of known tri-iodide concentration increases is created. The amount of total chlorine present in the water under test is proportional to the difference in tri-iodide concentrations from subsequent cycles as described above.

In some embodiments, the concentration of total chlorine in the water under test is determined from (a) a background voltage or current measurement, (b) a baseline voltage or current measurement, and (c) from one to about twenty cycles of (i) generating tri-iodide by application of current to the generation circuit and (ii) measuring the resulting voltage in the detection circuit. The choice of the number of cycles in step (c) will reflect a balance between accuracy of the total chlorine determination and the amount of time required to perform the analysis. More cycles generally lead to more accurate results. However, each cycle can take from several seconds to several minutes depending on operating parameters, and thus in the interest of providing efficient and safe dialysis, the fewest number of cycles in step (c) required to provide an accurate total chlorine determination is desired in one embodiment. Thus, in some embodiments, step (c) includes one to five cycles. In some embodiments, a first determination of total chlorine includes a larger number of cycles in step (c), while subsequent determinations of total chlorine include fewer cycles in step (c). For example and without limitation, a first determination of total chlorine in water under test includes three, four or five cycles in step (c). A subsequent or a plurality of subsequent total chlorine determinations then includes one, two or three cycles in step (c).

In some embodiments, the water sample is a purified water sample, for example a sample of water that has been passed through a filter comprising carbon. In some embodiments, the water sample is a sample of dialysis water produced by a water purification machine.

In some embodiments, the testing system is in fluid communication with a water purification machine, which is in turn in fluid communication with a dialysis machine. In some embodiments, the dialysis machine is configured to stop or prevent a dialysis treatment if the testing system determines that the total chlorine level of the sample of dialysis water produced by the water purification machine exceeds a predetermined level (e.g., about 0.1 ppm). In some embodiments, the testing system is configured to trigger an alarm or a notification on a display associated with the water purification machine and/or the dialysis machine indicating that the total chlorine level of the dialysis water exceeds a predetermined level (e.g., 0.1 ppm).

In some embodiments, the testing system includes a self-diagnostic feature capable of identifying a fault in the testing system. In one embodiment, the self-diagnostic feature compares a series of lag times between tri-iodide generation and tri-iodide detection over time to identify a fault in the testing system. In some embodiments, the self-diagnostic feature triggers an alarm indicating the fault state when the lag times exceed a predetermined level or increase beyond a predetermined level.

It is accordingly an advantage that the water purification system and method of the present disclosure is performed automatically.

It is another advantage that the water purification testing system and method of the present disclosure is calibrated automatically.

It is a further advantage that the water purification testing system and method of the present disclosure is cleaned automatically.

It is yet another advantage that the water purification testing system and method of the present disclosure is accurate.

It is yet a further advantage that the water purification testing system and method of the present disclosure is low cost.

It is still another advantage that the water purification testing system and method of the present disclosure is built into or packaged with a water purification system.

It is yet a further advantage that the water purification testing system and method of the present disclosure requires minimal maintenance.

Still another advantage is that the water purification testing system and method of the present disclosure reduces user interaction.

Still a further advantage is that the water purification testing system and method of the present disclosure outputs electrically for system integration.

Additional features and advantages are described herein, and will be apparent from, the following Detailed Description and the figures.

BRIEF DESCRIPTION OF THE FIGURES

FIG. 1 is a schematic view of one embodiment of a water purification testing system and method of the present disclosure.

DETAILED DESCRIPTION

Figure 3:
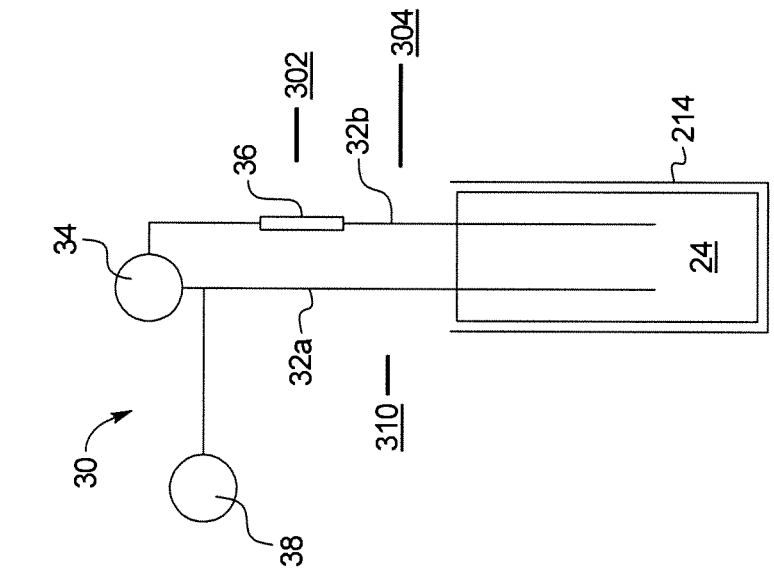
FIG. 3 is a schematic view of one embodiment of a detection cell of the present disclosure.

As discussed above, a more accurate and easier to use total chlorine sensor is needed to minimize the occurrences of false positives or trips inherent with other chlorine testing methods (e.g., testing strips). False positive results are problematic in the purification of water for hemodialysis because they force users to stop treatment and perform maintenance. False negatives may result in an unsafe treatment being performed. The testing system and method discussed herein greatly reduces the false tripping, can detect at least as low as 0.05 parts per million ("ppm") total chlorine concentration in one implementation, provides an automatic detection function (including calibration), built-in packaging, and the ability to be implemented with a relatively small incremental cost. In other embodiments, the testing system and method is capable of detecting 0.01 ppm total chlorine.

As used herein, the term, "total chlorine" refers to any and all reactive chlorine compounds including, but not limited to, chlorine gas (e.g., dissolved chlorine gas), hypochlorite, chloramines, and chloramine-T. Total chlorine may but does not have to exclude chloride salts (e.g., metal chlorides such as sodium chloride, potassium chloride, etc.).

In one embodiment, the water purity testing apparatus and associated methodology are integrated into a water purification machine, such as one set forth in U.S. Patent Publication No. 2011/0197971, entitled, "Water Purification System And Method", filed Apr. 25, 2011, which is in turn used with an online hemodialysis machine, such as one set forth in U.S. Patent Publication No. 2009/0101549, entitled, "Modular Assembly For A Hemodialysis System", filed Aug. 27, 2008, the entire contents of each of which are incorporated herein by reference and relied upon. The electrical and/or computer control units discussed below may be located in the water purification machine and/or the dialysis machine. The pumps and valves discussed below are located in one embodiment within the water purification machine. Thus, there can be electrical cabling running from the dialysis machine to the water purification machine to control the pumps and valves located within the water purification machine. Alternatively, the water purification machine can also house its own electrical and/or computer control unit for controlling the purification units, pumps and valves. Even here, however, the water purification control unit can communicate wired or wirelessly with the dialysis machine and be subordinate, for example, to the dialysis machine's master controller, e.g., sending chlorine data to same. Either one or both of the control units of the dialysis unit or the water purification unit could then place the overall system into an alarm state if needed.

In one embodiment, the system and method of the present disclosure measure chlorine indirectly by allowing the molecule to oxidize iodide to tri-iodide and measuring the corresponding voltage change. Total chlorine may be introduced into the system through many forms including, but not limited to, chlorine standard free chlorine (e.g., $Cl_2$ dissolved in water), hypochlorite (e.g., as bleach), or chloramine-T. In a preferred embodiment, chloramine-T is used as a stabilized form of total chlorine and is added to an iodide-containing reagent solution. Chloramine-T degrades to hypochlorite and hypochlorite in turn reacts with iodide via the following relationship to form tri-iodide:

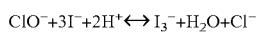

$$ClO^- + 3I^- + 2H^+ \leftrightarrow I_3^- + H_2O + Cl^-$$

Calibration of the electrode system is achieved by electrochemically generating tri-iodide and measuring the system response (voltage). Tri-iodide may be generated in multiple sessions to improve the estimation of the dependence of voltage with changes in tri-iodide concentration. The amount of tri-iodide generated is computed from measured current moving though the electrode placed into a potassium iodide chamber. The current, in turn, is determined by measuring the voltage change across a resistor of known value. Tri-iodide generation can be accomplished using metals including, but not limited to, platinum and stainless steel, and by using $SO_4^{-2}$ as an auxiliary electrolyte. In this scenario, the electrochemical equations governing the generation of tri-iodide are:

$$3I^- \rightarrow I_3^- + 2e^-$$

$$SO_4^{-2} + 2e^- + 4H^+ \rightarrow SO_2 + 2H_2O$$

In one preferred embodiment, sulfate ions are introduced through sodium sulfate and iodide ions are introduced as potassium iodide. Sodium sulfate concentrations and potassium iodide concentrations above 5 g/L have been seen to yield reproducible generations of tri-iodide molecules. Also in a preferred embodiment, the generation voltage is maintained by a voltage source set to deliver 700 mV. The corresponding generating voltage ranges from 0.5 to 3.5 V and depends on the concentration of iodide and sulfate ions.

Referring now to the drawings and in particular to FIG. 1, in one embodiment an, e.g. embedded, testing system 10 provides two reagent reservoirs including an iodide reservoir or cell 12 and a reducing agent reservoir or cell 14. Iodide reservoir or cell 12 includes an iodide source. Any iodide source may be used, provided that the iodide source completely dissociates in water. Non-limiting examples of iodide sources include alkaline iodide reagents such as potassium iodide (KI) and/or sodium iodide (NaI). Reducing agent reservoir or cell 14 includes a reducing agent. Any suitable reducing agent may be used, provided that the reducing agent readily accepts electrons. One non-limiting example of a reducing agent is an alkaline sulfate such as sodium sulfate ($Na_2SO_4$). In one embodiment, iodide reservoir or cell 12 includes potassium iodide and reducing agent reservoir or cell 14 includes sodium sulfate. System 10 also includes a main testing unit 20 that operates with two electrical control circuits 30 and 40. Main testing unit 20 includes a liquid-tight housing 22, which is separated into two compartments 24 and 26 by a semi-permeable membrane 28 to allow charged ions to pass through the membrane, preventing an open circuit. Housing 22 can be metal or plastic as desired. Compartments 24 and 26 can be opened or closed and be sized to be the same or to have different volumes as desired. Membrane 28 can be a semipermeable membrane made of a suitable material including polyether sulfone, cellulose, nylon, and/or any other semipermeable membrane with a molecular weight cut-off ("MWCO") of about 1,000 Daltons, in one preferred embodiment about 500 Daltons, and in another preferred embodiment from about 100 Daltons to about 500 Daltons. In some embodiments, membrane 28 is Ultracel PL-1 from Millipore (MWCO 1000). In some embodiments, the membrane allows only positive charge to penetrate. In some embodiments, the membrane allows only negative charges to penetrate. In some embodiments, the membrane allows both positive and negative charges to penetrate.

Reagent reservoirs 12 and 14 are both in valved and pump communication with main testing unit 20. In an embodiment, the iodide reservoir 12 and/or the reducing agent reservoir 14 are provided in a cartridge or cassette form. In an embodiment, the cartridge or cassette includes iodide reservoir 12 and reducing agent reservoir 14. In another embodiment, the cartridge includes iodide reservoir 12, reducing agent reservoir 14, and electrodes 42a and 42b for tri-iodide generation circuitry 40 and/or electrodes 32a and 32b for tri-iodide detection circuitry 30. In an embodiment, the iodide is provided in a liquid form such as a pre-mixed solution or a concentrate, or in a solid form such as a crystal, a powder, and/or a tablet. In an embodiment, the reducing agent is provided in a liquid form such as a pre-mixed solution or a concentrate, or in a solid form such as a crystal, a powder, and/or a tablet. When either chemical is provided in dry form, the associated control unit can control the associated pumps and valves to first pump water into the crystal, dry powder or tablet containers for mixing before pumping liquid iodide or reducing agent from the containers.

In the embodiment illustrated in FIG. 1, the iodide cell or reservoir 12 communicates fluidly with the iodide and sample chamber or compartment 24 of main testing unit 20 via line 52a including a valve 16a and pump 18a. Reducing agent cell or reservoir 14 in turn communicates fluidly with chamber or compartment 26 of main testing unit 20 via line 52b including valve 16b and pump 18b.

FIG. 1 also illustrates that the main testing unit 20 is fluidly connected to a water purification unit or machine 50, which can be the water purification machine described above in the incorporated U.S. 2011/0197971 Publication. In the illustrated embodiment, there are multiple connections between water purification machine 50 and main testing unit 20. In particular, test water is pumped from a test water outlet or supply 58 of water purification machine 50 to KI and sample chamber or compartment 24 of main testing unit 20 via line 52c, including valve 16c and pump 18c. Deionized ("DI") water is pumped from DI water outlet or supply 56 of water purification machine 50 to iodide and sample compartment 24 of main testing unit via line 52d, including valve 16d and pump 18d. Drainage water is pumped from the iodide and sample compartment 24 of main testing unit 20 to a drain 54 of water purification machine 50 via line 52e, including valve 16e and pump 18e.

Drainage water is also pumped from reducing agent chamber or compartment 26 of main testing unit 20 to drain 54 of water purification machine 50 via line 52f, including valve 16f and pump 18f. DI water is also pumped from DI water outlet or supply 56 of water purification machine to reducing agent compartment 26 of the main testing unit via line 52g, including valve 16g and pump 18g.

In an alternative embodiment, a single drain pump (18e or 18f) is used instead of the separate drain pumps illustrated and drain valves 16e and 16f are sequenced to selectively drain from one or both of chambers or compartments 24 and 26. Alternatively or additionally, a single DI pump (18d or 18g) is used instead of the multiple DI pumps illustrated and DI valves 16d and 16g are sequenced to selectively pump DI water to one or both of chambers or compartments 24 and 26. Thus, the number of pumps shown in FIG. 1 can be reduced by at least two pumps from the number of pumps illustrated.

As described in further detail below, chlorine testing is performed using the valves and pumps provided or operable with lines 52a to 52c in association with the control circuit 30 and electrode pair 32a and 32b. Calibration is performed using the valves and pumps provided or operable with lines 52a, 52b, 52d and 52g in association with control circuits 30 and 40 and their respective electrode pairs 32a/32b and 42a/42b. Rinse is performed using the valves and pumps provided or operable with lines 52d to 52g.

In an embodiment, pumps 18*a* to 18*g* are electrically operated pumps, such as microfluidic pumps, and can be gear, centrifugal, piston or vane pumps. The pumps may have liquid contacting surfaces that are made of medical grade plastic or stainless steel, such that the surfaces cannot themselves corrode or contaminate water, such as test, DI or drain water, running past the surfaces, or they may have liquid contacting surfaces that may contaminate the fluid if placed in the drain line. In an alternative embodiment, pumps 18*a* to 18*g* are small peristaltic (roller or linear) or tube actuating (e.g., shuttle) pumps that pump water, such as test, DI or drain water, through a respective tube by collapsing, squeezing and/or crushing the tube sequentially to move the fluid. In another alternative embodiment, pumps 18*a* to 18*g* are electrically and/or pneumatically actuated membrane pumps that move water, such as test, DI or drain water, by fluctuating a membrane back and forth between a chamber of known volume. Pumps 18*a* to 18*g* can further alternatively be any combination of the above types of liquid pumps, selected to optimize performance, cost and reliability.

It should be appreciated from the above discussion of the various types of pumps 18*a* to 18*g*, that lines 52*a* to 52*g* can be made of different materials, such as stainless steel or plastic. Suitable plastics include polyvinylchloride ("PVC"), for example, when lines 52*a* to 52*g* do not have to be deformed for, e.g., peristaltic or shuttle, pumping, or silicone, for example, when lines 52*a* to 52*g* are deformed for, e.g., peristaltic or shuttle, pumping. If membrane pumps are used, lines 52*a* to 52*g* may contain sections that transition to a chamber having membrane sheeting, which can likewise be plastic, such as PVC sheeting.

Each of valves 16*a* to 16*g* can be an electrically or pneumatically actuated valve. In an embodiment, valves 16*a* to 16*g* include a valve housing to which the respective line 52*a* to 52*g* is sealingly attached. Here, each line 52*a* to 52*g* can be broken and sealingly attached to inlet and outlet connectors of the respective valve 16*a* to 16*g*. Also, here the valve includes its own internal opening/shutting mechanism. Alternatively, valves 16*a* to 16*g* are electrically or pneumatically actuated solenoid valves that operate directly on lines or tubes 52*a* to 52*g*, e.g., compressible plastic tubes. The solenoid valves can for example be fail-safe or spring-operated closed and electrically or pneumatically actuated open. In a further alternative embodiment, valves 16*a* to 16*g* are electrically and/or pneumatically actuated membrane valves, for example, provided as part of a disposable cassette that includes a hard, valve chamber part that is sealed fluidly by one or more flexible, e.g., PVC, sheet that is flexed to close and open the hard part of the chambers. Here, the hard part can also be formed with pump chambers and the same one or more flexible sheet can be used for pumps 18*a* to 18*g*. Valves 16*a* to 16*g* can further alternatively be any combination of the above types of liquid valves, selected to optimize performance, cost and reliability.

System 10 includes a control unit 60, which in the illustrated embodiment is housed inside water purification machine 50. Control unit 60 can include one or more processor, one or more memory and one or more control circuitry, such as control circuits 30 and 40. Pumps 18*a* to 18*g* and valves 16*a* to 16*g* can be operated under the control of a computer program stored at control unit 60. Control unit 60 is in one embodiment the same control unit 60 used for all of water purification machine 50. Hence, control unit 60 may include a master processor that communicates (i) with a user interface 62 of water purification machine 50, (ii) with a wired or wireless data link to a corresponding control unit 110 of dialysis machine 100 that uses water produced by water purification machine 50, and (iii) with one or more delegate processor that runs the electrical equipment provided within water purification machine 50, including pumps 18*a* to 18*g* and valves 16*a* to 16*g*. Either one or both of the master and delegate processors of control unit 60 may receive signal inputs from and send signal outputs to control circuits 30 and 40.

In one embodiment, the master processor sends output data, such as chlorine content output data, to one or both of a user interface of water purification machine 50 and/or to the control unit 110 of the dialysis machine 100. It is contemplated for dialysis machine 100 to sit on top of water purification machine 50. Thus, either user interface 62 of water purification machine 50 and/or user interface 112 of dialysis machine 110 could be used to inform the patient or caregiver of the chlorine results and to communicate any associated alerts or alarms. In one embodiment, however, main user interface 112 of dialysis machine 110 is a wireless, e.g., tablet, user interface that allows the patient or caregiver to reside remotely from the dialysis machine while still viewing information concerning same. Here, it is desirable to send water purification machine 50 data, such as chlorine contest data, via control unit 60 to control unit 110 of dialysis machine 100, which in turn forwards the pertinent data to remote user interface or tablet 112.

In an alternative embodiment, the generation and receipt of signals to and from control circuits 30 and 40 and the control of pumps 18*a* to 18*g*, valves 16*a* to 16*g* and possibly other electrical components of water purification machine 50 is done via control unit 110 of the dialysis machine 100. Here again, control unit 110 of dialysis machine 100 can forward pertinent data to the remote user interface or tablet 112 of the dialysis machine 100. When control unit 110 of machine 100 is the primary control unit for water purification system 10, control unit 60 may be eliminated, at least as far as system 10 is concerned, or limited to a smaller number of tasks.

In any case, control unit 60 and/or control unit 110 opens valves 16*a* to 16*g* and operates pumps 18*a* to 18*g* to meter into compartments 24 and 26 precise amounts of desired fluids, e.g., DI water, iodide solution, reducing agent solution or test water solution, or to remove precise amounts of fluids from chambers or compartments 24 and 26 to drain 54. The metering can be run open loop and rely on the accuracy of the pumping mechanism to deliver the correct ratio of fluids. Alternatively or additionally, feedback in the form of conductivity sensing may be used to ensure that the proper proportioning of fluids takes place within chambers or compartments 24 and 26.

As illustrated, in an embodiment, main unit 20 is placed in fluid communication with deionized water via outlet or storage 56 from water purification unit 50. Deionized water is pumped into the main unit (e.g., into the chambers or the compartments 24 and 26 separately) to flush the water test sample and any residual tri-iodide and/or total chlorine from the main unit. In some embodiments, the total chlorine level is determined before and/or during each dialysis treatment. Here, an aliquot of water from water purification unit 50 for making dialysate is diverted to system 10 and analyzed by the methods disclosed herein before any water from purification unit 50 is allowed to be used to make dialysate at machine 100. Control unit 60 or 110 can be programmed to prevent and/or suspend dialysis fluid preparation when the total chlorine level in the dialysis water exceeds a threshold level, for example 0.1 ppm. In some embodiments, water from purification unit 50 is analyzed after a dialysis treatment is completed, such that corrective action can be taken to reduce total chlorine levels in the water before a subsequent dialysis treatment is required, and providing typically at least twenty-four hours before the subsequent treatment.

As discussed above, system 10 can be implemented within water purification unit 50. If so, main unit 20 can be positioned downstream of one or more filter used in water purification unit as specified in the U.S. 2011/0157971 Publication. For example and without limitation, main unit 20 may be in fluid communication with a carbon filter, wherein water exiting the carbon filter, or samples thereof, is then tested for total chlorine compounds according to the present disclosure. A failed test likely means that the carbon filter is faulty or spent and needs replacement. A suitable message can then be displayed, e.g., on user interface 112 of dialysis machine 100.

Electrical circuit 40 operates via a pair of electrodes 42a and 42b to perform calibration. Electrode 42a is inserted into iodide and sample compartment 24, while electrode 42b is inserted into reducing agent chamber or compartment 26. Electrodes 42a and 42b can be metallic. In some embodiments, electrodes 42a and 42b are each provided with or are in electrical communication with a resistor (e.g., a 1 kΩ resistor). As described above, the iodide solution and the reducing agent solution are separated by membrane 28, which permits electricity but not fluid to flow across the membrane. In one embodiment, membrane 28 includes micropores or perforations in the membrane, which are formed such that there are about three (3) to about twenty (20) holes, each hole sized such that charge can freely pass between the chambers without any fluid passing between the chambers. In one example embodiment, the membrane is formed of a silicone elastomeric material and includes about seven micropores formed by a 28-gauge needle. The elastomeric nature of the membrane causes the holes to substantially close, allowing electrical charge to pass through without permitting fluid to pass between the chambers. One suitable membrane 28 is made of silicone tubing. Another suitable membrane 28 is provided by Millipore and is sold under the trade name ULTRACEL PL-1. When a voltage is applied to electrical circuit 40 (e.g., about 1 volt DC), the induced current generates tri-iodide from the iodide solution.

As discussed above, system 10 includes electrical control circuits 30 and 40. Electrical circuit 30 operates via a pair of electrodes 32a and 32b, which are each inserted into iodide and sample chamber or compartment 24 of main testing unit 20.

Electrical circuit 30 detects the amount of tri-iodide generated at or by electrical control circuit 40. In some embodiments, electrical circuit 30 is a tri-iodide detection circuit in which each electrode 32a and 32b is carbon-based or metallic (e.g., metallic, platinum, stainless steel, gold, combinations and alloys thereof). At least one of the electrodes 32a or 32b can include or be in electrical communication with a resistor (e.g., a 5 kΩ resistor). In the illustrated embodiment, both electrodes 32a and 32b are in contact with the fluid held within iodide and sample compartment 24. When a low voltage is applied across electrodes 32a and 32b, the current induced can be measured and used as a proxy for the amount of tri-iodide in the solution, and therefore the amount of total chlorine in the water sample. In some embodiments, the system 10 formulated as just described is capable of determining an amount of total chlorine in the water sample as low as about 0.1 ppm.

Figure 2:
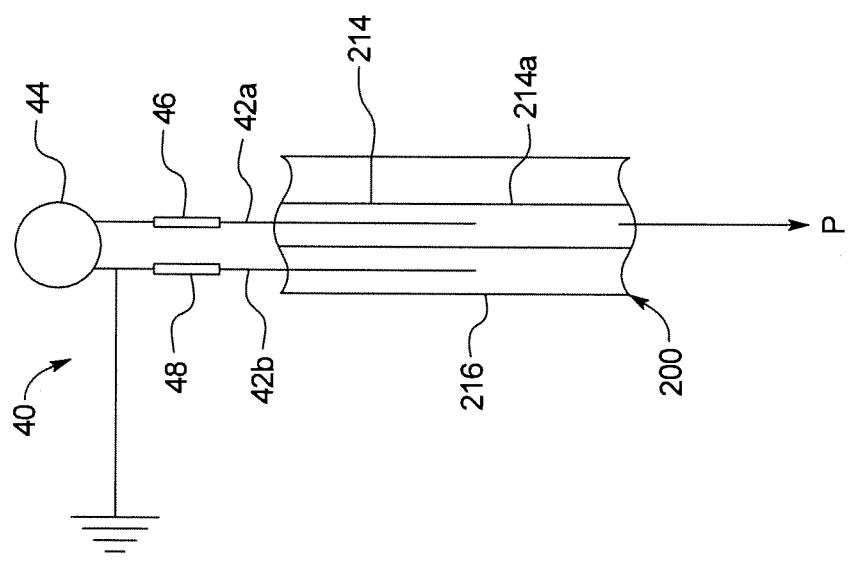
FIG. 2 is a schematic view of one embodiment of a generation cell of the present disclosure.

In one embodiment shown in the sectioned view of FIG. 2, testing unit 20 is provided, at least in part, as a tubing assembly 200. The iodide and sample chamber or compartment 24 is a tube 214 disposed within a reducing agent chamber or compartment 26, which is also a tube 216, and which is of a larger diameter than that of tube 214 (chamber 24). In some embodiments, the outer reducing agent tube 216 has an inner diameter that is about 1.5 to about 4 times larger the outer diameter of the inner iodide and sample tube 214. Tube 214 (chamber 24) is in fluid communication with iodide reservoir 12 (not illustrated in FIG. 2), while tube 216 (chamber 26) is in fluid communication with reducing agent reservoir 14 (not illustrated in FIG. 2). The inner iodide and sample tube 214 includes or defines a plurality of perforations 214a (membrane 28), e.g., hydrophobic perforations, which do not allow fluid to pass between chambers 24 and 26, but permit electrical conductivity to flow between the chambers (through the wall of narrower tube 214 into the outer diameter of larger tube 216).

The inner iodide and sample tube 214 is also in fluid communication with water to be tested (not illustrated in FIG. 2), which is pumped via line 52c and pump 18c from test sample outlet 58 of water purification machine 50. The tri-iodide generation loop of electrical circuit 40 includes electrodes 42a and 42b, each having or being in electrical communication with a respective resistor 46 and 48 (e.g., a 1 kΩ resistor). Electrode 42a of electrical circuit 40 is placed in contact with the fluid in the inner iodide and sample tube 214, while the other electrode 42b is placed in contact with the fluid in the outer reducing agent tube 216. In the illustrated embodiment, electrode 42b is grounded. As mentioned above, electrodes 42a and 42b can be formed of durable metal such as platinum, stainless steel, gold, copper, or be combinations or alloys thereof.

A voltage source 44 is provided (e.g., as part of electronics 40 or as part of control unit 60 or 110) to apply a voltage, such as from about 0.7 VDC to about 1.0 VDC. The voltage source across the set resistance of resistors 46 and 48 generates a desired current. The applied current generates tri-iodide in the iodide and sample tube 214 (chamber 24).

The tri-iodide generated by tri-iodide generation circuit 40 travels along pathway P (shown in FIG. 2) towards tri-iodide detection cell 30, one embodiment of which is shown in FIG. 3. Tri-iodide detection cell 30 includes two electrodes 32a and 32b. In some embodiments, electrodes 32a and 32b are formed of carbon or a durable metal, such as platinum, stainless steel, gold, copper, or combinations or alloys thereof, and are in contact with the fluid in the iodide and sample compartment 24 provided here by inner tube 214. Electrode 32b includes or is in electrical communication with a resistor 36, which may be for example a 5k9 resistor. In some embodiments, electrodes 32a and 32b are shielded or coated in a manner such that the proportion of the electrodes exposed to fluid remains constant throughout the testing process even if iodide and sample compartment 24 is moved somehow relative to the electrodes. Application of a low voltage (e.g., about 100 mVDC) from a voltage source 34 (e.g., of electronics 30 or of control units 60 or 110) induces a current across electrodes 32a and 32b and the set resistance of resistor 36. The voltage across the resistor 36 is measured and stored and/or recorded, e.g., at control unit 60 or 110, and is used to calculate the current across electrodes 32a and 32b. The voltage (or calculated current) is proportional to the amount of tri-iodide generated by the tri-iodide generation circuit 40. In one embodiment, the voltage measured in the tri-iodide detection cell 30 is a steady state voltage. Sensor 38 can be configured to output to control unit 60 or 100.

In one embodiment, iodide reservoir 12 is a chamber holding an alkaline iodide solution of known concentration (for example a solution having a known amount of an alkaline iodide such as KI and/or NaI in a known amount of water), and which is in fluid communication with the iodide and sample chamber 24 as shown and discussed above. In some embodiments, iodide reservoir 12 holds about 0.1 gram to about one gram of iodide salt(s) (e.g., an alkaline iodide such as KI and/or NaI) in about one to about ten mL of water. In some embodiments, the iodide solution is a solution of 0.25 gram to 0.7 grams of iodide salt(s) (e.g., an alkaline iodide such as KI and/or NaI) in three to seven mL of water. In some embodiments, iodide reservoir 12 contains at least enough iodide salt(s) to last about one month or longer, e.g., from one month to six months, for example, so that refilling iodide reservoir 12 does not reduce the normal maintenance cycle of water purification unit 50. In some embodiments, the iodide solution itself has a level of total chlorine that is below the detection limit for the system. In some embodiments, the iodide solution has less than 0.1 ppm, less than 0.05 ppm, or less than 0.01 ppm of any total chlorine compound.

Reducing agent reservoir 14 is a chamber holding a solution including a known amount of one or more reducing agents (e.g., an alkaline sulfate such as $Na_2SO_4$). In some embodiments, the reducing agent reservoir includes about two to about twenty grams of reducing agent (e.g., an alkaline sulfate such as $Na_2SO_4$) in a suitable amount of water. In some embodiments, the reducing agent reservoir 14 holds about seventeen grams of $Na_2SO_4$. In some embodiments, reducing agent reservoir 14 contains at least enough reducing agent (e.g., an alkaline sulfate such as $Na_2SO_4$) to last about one month or longer, e.g., from one month to six months, for example, so that again refilling reducing agent reservoir 14 does not reduce the normal maintenance cycle of water purification unit 50.

In an embodiment, tri-iodide is generated in a water test sample by the tri-iodide generation circuitry 40 according to the parameters shown in the following Table 1. In such an embodiment, resistors 36, 46 and 48 are each 1 kΩ, and the liquid impermeable silicone elastomeric membrane (e.g., at 28 or 214a) includes nine holes each formed by piercing the membrane with a 28-gauge needle, the holes then substantially closing due to the compressive elasticity of the membrane as described above. The concentration of iodide in the iodide reservoir 12 in the example is 66,667 ppm, with potassium iodide (KI) or another iodide source dissolved in water such that the total iodide solution volume is 4 mL in compartment 24. The concentration of the reducing agent in the reducing agent reservoir 14 is about 75,000 ppm, with sodium sulfate or another reducing agent dissolved in water. A voltage of about 0.7 VDC is applied across circuit 40 for about one minute.

Generation Cell Specifications

TABLE 1

| Parameter | Value |
| --- | --- |
| Voltage | 0.7 V |
| Generation Time | 1 minute |
| Resistor | 1 kΩ (0.983 kΩ) |
| Perforations | 9 holes produced by a 28-gauge needle |
| Potassium iodide volume | 4 mL (shared with detection cell) |
| Potassium iodide concentration | 66,667 ppm |
| Sodium sulfate concentration | 75,000 ppm |

In one example, the tri-iodide concentration is determined using a tri-iodide detector cell 30 having the parameters shown in Table 2. A voltage of about 0.1 VDC is applied for about five minutes across the tri-iodide detector cell having a 5 kΩ resistor. The induced current is measured by conventional current, or via voltage meter with known resistance, and compared against a standard curve to determine the total chlorine content of the water test sample. The standard curve is discussed in more detail below.

In an embodiment, the detector cell 30 continuously determines the voltage across the resistor 36. In such an embodiment, the detector cell 30 can also be used to diagnose one or more performance issue in the system 10. For example, due to mass transfer and based at least in part on the size of the chambers 24 and 26 and the identity and characteristics of membrane 28, a change (e.g., an increase) in a lag time between the application of a voltage to electrode pair 32a and 32b and the detection of an increase in voltage or current in the detector cell 30 may indicate failure of a pump (e.g., one or more of pumps 18a to 18f), a valve (e.g., one or more of valves 16a to 16f), the membrane 28, electrode pair 32a and 32b, electrode pair 42a and 42b, or a combination of the foregoing.

In an embodiment, control unit 60 or 110 automatically performs multiple total chlorine determinations and averages the discrete results. It is contemplated for system 10 to use an agitator, such as an ultrasonic vibrator to agitate testing unit 20 during the test cycle to promote connectivity between the tri-iodide generation loop 40 and the tri-iodide detection cell 30.

Detection Cell Specifications

TABLE 2

| Parameter | Value |
| --- | --- |
| Voltage | 0.1 V |
| Equilibration Time | 4 minute |
| Resistor | 5 kΩ (4.91 kΩ) |
| Potassium iodide volume | 4 mL (shared with generation cell) |
| Potassium iodide concentration | 66,667 ppm |

Example Methodology

Using system 10, control unit 60 or 110 can operate according to one methodology as follows:
(a) providing a total chlorine detection system as disclosed herein;
(b) providing a water sample, the water sample including an amount of total chlorine;
(c) measuring a background current in a tri-iodide detection circuitry or cell 30, the background current associated with tri-iodide present in the system before introduction of the water sample;
(d) metering an amount of the water sample into the system;
(e) generating a first amount of tri-iodide by the reaction of the total chlorine with iodine in the system;
(f) monitoring a baseline current in a tri-iodide detection circuitry or cell 30, the baseline current associated with the amount of tri-iodide in the water sample;
(g) generating a second, known amount of tri-iodide from the water sample by a tri-iodide generation circuitry or loop 40;
(h) monitoring a second current induced in a tri-iodide detection circuitry or cell 30, the second current associated with the sum of the first and second amounts of tri-iodide;
(i) generating a third, known amount of tri-iodide from the water sample by the tri-iodide generation circuitry or loop 40;

(j) monitoring a third current induced in the tri-iodide detection circuitry or cell 30, the third current associated with the sum of the first, second and third amounts of tri-iodide;

(k) optionally generating a fourth, known amount of tri-iodide from the water sample by the tri-iodide generation circuitry or loop 40;

(l) optionally monitoring a fourth current induced in the tri-iodide detection circuitry or cell 30, the fourth current associated with the sum of the first, second, third and optional fourth amounts of tri-iodide; and (m) calculating the total chlorine concentration in the water sample using the baseline current, the second monitored current, the third monitored current, and the optional fourth monitored current, wherein each of the currents is optionally corrected by first subtracting the background current.

The calculation step (m) can be accomplished using any suitable data analysis means based on one or more of the baseline current and first monitored current, second monitored current, optional third monitored current, and optional fourth monitored current. In an example methodology, calculating the total chlorine concentration in the water sample in step (m) above includes:

(i) plotting the first, second, third and optional fourth current values (y-axis), optionally corrected by subtracting the background current, as a function of relative tri-iodide concentration, wherein the first relative tri-iodide concentration as determined in step (f) is set to x=0; and (ii) extrapolating a line of best fit using at least two of the second, third and optional fourth current values (each optionally corrected by subtracting the background current) to a point where y is equal to the baseline current and correlating said point to determine the x-value ("$x_0$"), associated with said point, wherein the unknown total chlorine concentration is equal to $(-1)(x_0)$.

In some embodiments, control unit 60 or 110 can cause an amount of time between a monitoring step and a subsequent tri-iodide generating step (e.g., between steps (f) and (g), between steps (h) and (i), and/or between steps (j) and (k)) to be no less than one minute, for example from about one minute, anywhere to about ten minutes. In some embodiments, control unit 60 or 110 causes an amount of time between a tri-iodide generating step and the correlating current monitoring step (e.g., between steps (e) and (f), between steps (g) and (h), between steps (i) and (j), and/or between steps (k) and (l)) to be no less than about one minute, for example from about one minute, anywhere to about ten minutes. In some embodiments, control unit 60 or 110 causes current to be monitored in one or more of steps (f), (h), (j), and/or (l) for no less than one minute, for example from about one minute, anywhere to about ten minutes.

In any embodiment described herein, the monitored currents can be corrected to exclude any background tri-iodide present in the system by subtracting the background current from each monitored current value. In other embodiments, background tri-iodide present in, for example, the iodide reagent, can be reduced, minimized or eliminated by reversing the polarity of the tri-iodide generation electrode and applying a suitable voltage for a period of time sufficient to convert any background tri-iodide to iodide before introduction of a water sample.

In some embodiments, a mechanism is included to adequately mix water under test with the iodide reagent. For example, the testing system may include an agitator, a vibration mechanism, one or more baffles, a stirrer, or any other suitable stirring mechanism. The mixer can be invasive, such as a rotating mixer, or be non-invasive, such as a vibrator that vibrates the outside of the reservoir.

In one ideal implementation, control unit 60 or 110 causes one unit (e.g., mole) of tri-iodide to be generated for each unit (e.g., mole) of total chlorine. In some embodiments, control unit 60 or 110 causes the pump speeds of one or more or all of concentrate pumps 18a and 18b and test sample pump 18c to be adjusted to optimize the ratio of the moles of tri-iodide formed per moles of total chlorine in the water under test. In some embodiments, a higher pump speed generates closer to about one mole of tri-iodide per mole of total chlorine than a slower pump speed under otherwise identical conditions.

In some embodiments, chloramine-T is used as an artificial total chlorine source to optimize or calibrate pump speed based on the measured current in the tri-iodide detection cell. In such embodiments, a water sample with known total chlorine concentration may be prepared by combining a water sample with no or essentially no total chlorine content with a known amount of chloramine-T. The resulting water sample having a known total chlorine concentration may then be used to test the sensor, calibrate the system, or optimize pump speed.

In some embodiments, the testing system can be manually calibrated using a series of water samples each having a known amount of total chlorine (e.g., a series of chloramine-T solutions of known concentration). In such embodiments, the testing system can be manually calibrated, and the testing method may include (a) determining a background voltage or current measurement, and (b) determining an amount of total chlorine in water under test by (i) monitoring a baseline current in the detection circuit, (ii) generating tri-iodide by application of current to the generation circuit, (iii) measuring the resulting voltage in the detection circuit, and (iv) comparing the voltage measured in the detection circuit to the manually-derived calibration curve to calculate the amount of total chlorine in the water under test.

Determination of the total chlorine content of the water test sample is sensitive to the volume of the water test sample provided. Accordingly, in an embodiment, the amount of test sample water is accurately metered and/or pumped into main test unit 20 by, for example, a microfluidic pump as discussed above. One suitable microfluidic pump is the SmoothFlow™ by Microfluidica, LLC (Glendale, Wis.). Although any amount of water under test may be used, typically a small volume, for example from about 50 µL anywhere to about 500 µL of water under test is pumped into main testing unit 20.

Figure 4:
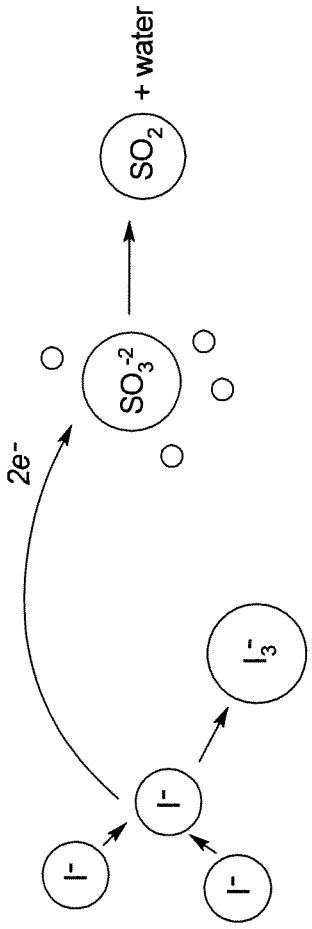
FIG. 4 is a schematic view of one representation of a mechanism in which a sodium sulfate anion promotes the conversion of three iodide anions to one tri-iodide anion and two electrons in water.

FIG. 4 illustrates the principle of the electrochemical reaction. In aqueous solution, one equivalent of sulfate ($SO_4^{-2}$) promotes the conversion of three iodide anions (I⁻) to one tri-iodide anion ($I_3^-$). The process consumes four equivalents of protons while producing one equivalent of $SO_2$ and one equivalent of water, and simultaneously liberating two electrons ($e^-$). When iodide anions are present in excess compared to the amount of total chlorine, the amount of tri-iodide produced is directly proportional to the amount of total chlorine present.

Figure 5:
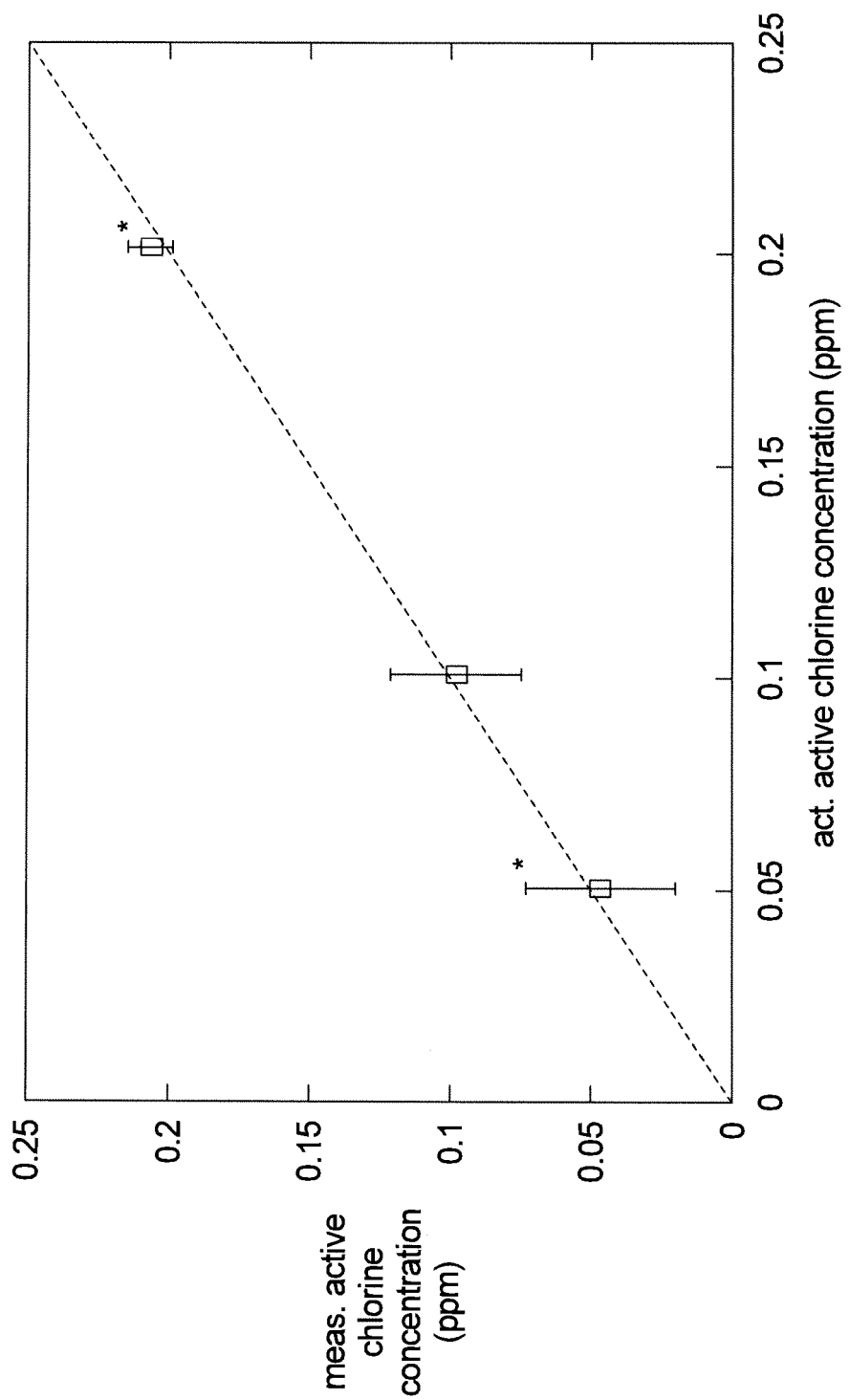
FIG. 5 is a graph showing chlorine concentration measured by a water purification testing system and method of the present disclosure versus actual chlorine concentration.

FIG. 5 demonstrates the accuracy of one embodiment of the presently disclosed system and method using chloramine-T as an artificial source of total chlorine in water under test. The chlorine content of three test solutions of known chlorine concentration (0.05 ppm, 0.1 ppm and 0.2 ppm) were determined using the parameters of Tables 1 and 2 above. As shown in FIG. 5, system 10 and the corresponding method are accurate even for ultra-low chlorine concentrations (e.g., 2 ppm total chlorine or less). The dashed line shows the ideal measurement (slope=1). The system is accurate within 3% at 0.1 and 0.2 ppm, and within 8% at 0.05 ppm. Error bars indicate 95% confidence levels at each data point.

In an embodiment, the total chlorine content of the water under test can be calculated by any analytical means from the baseline current and the one or more tri-iodide-related current values. For example, the concentration of tri-iodide generated ($[I_3^-]$) can be determined from the current (i) according to the following relationship:

$$[I_3^-]=i*t/2F*V,$$

where i=current (A or charge/s), t=time (s), F=Faraday's constant (charge/mole of electrons), V=iodide reagent solution volume in liters, and 2 represents the number of electrons transferred between iodide and tri-iodide.

Figure 6:
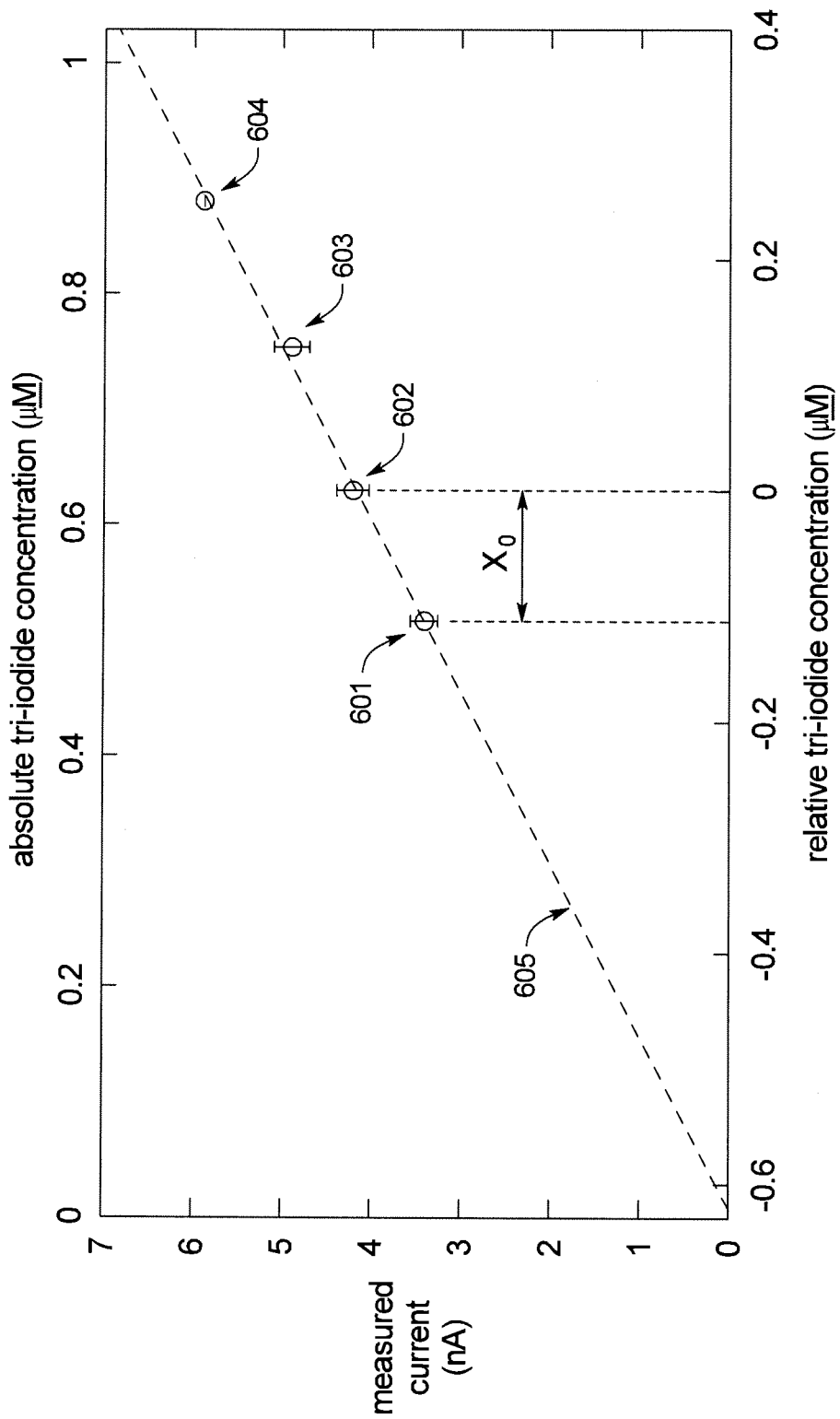
FIG. 6 is a graph showing an example calculation of a total chlorine level for a water sample according to the present disclosure.
Figure 7:
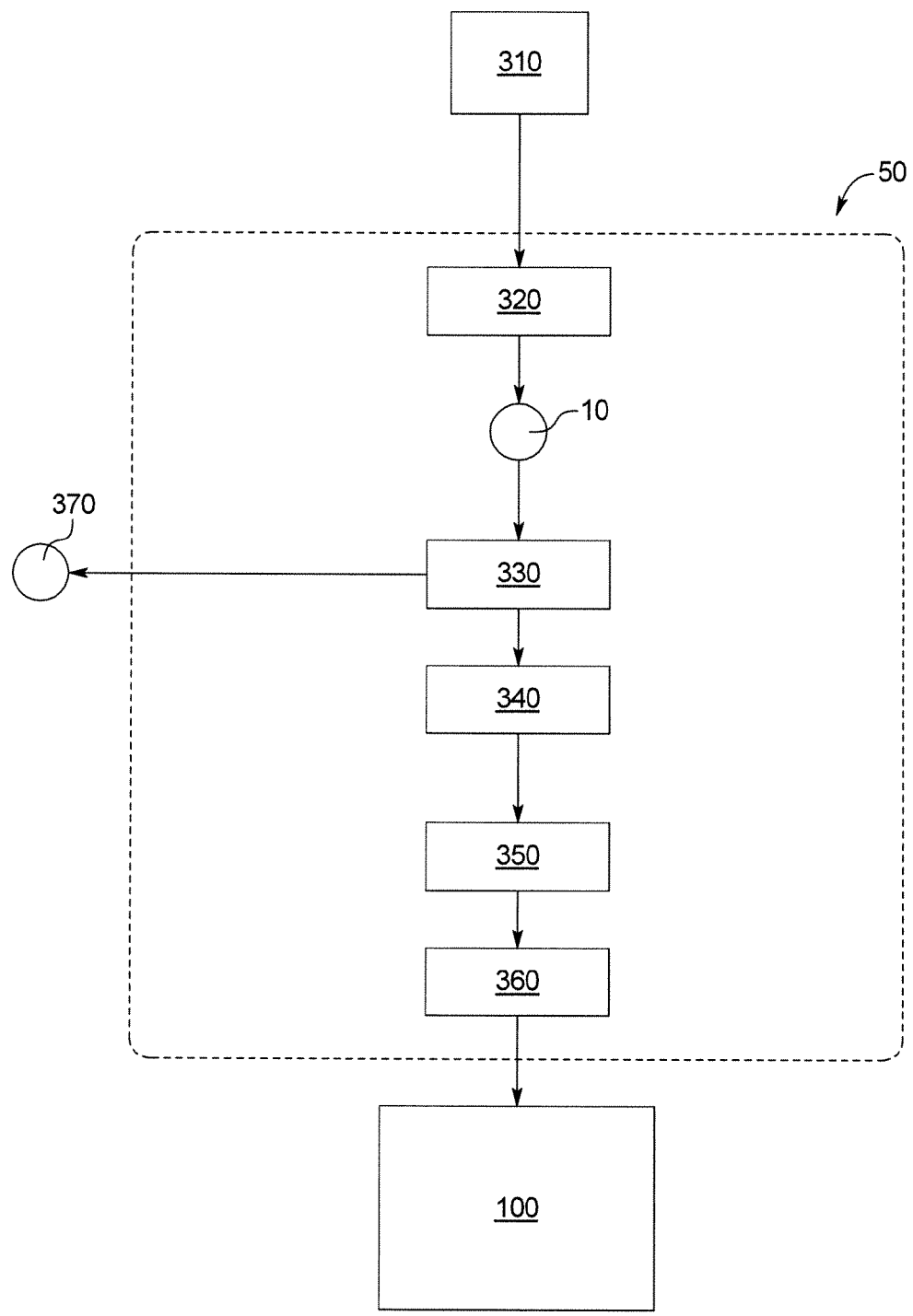
FIG. 7 is a schematic view of one embodiment of a water treatment system which includes a detection cell of the present disclosure.

FIG. 6 shows an example chlorine determination according to the process described above. The baseline current corresponds to baseline point 601. Point 602 corresponds to the first current and first tri-iodide concentration. Point 603 corresponds to the second current and second tri-iodide concentration. Point 604 corresponds to the third current and third tri-iodide concentration. A standardized curve or line of best fit 605 is determined using points 602, 603 and 604. The concentration of chlorine ($x_0$) in the water under test is determined by determining the x-intercept of line of best fit 605 for baseline current 601.

Example Operation

Using system 10, one example operation stored at control unit 60 or 110 is as follows:

Step 1. Add 0.25 gram to 0.7 gram of KI and three mL to seven mL of water to the KI reservoir, and two grams to twenty grams of $Na_2SO_4$ and 225 mL water to the $Na_2SO_4$ reservoir.

Step 2. 200 µL of water under test are then pumped via a microfluidic pump into the KI/water sample chamber of the main unit.

Step 3. 700 mV is then applied to electrode pair 42a and 42b to generate tri-iodide. Optionally, the main unit is agitated to promote mass transfer between the electrode pairs 32a/32b and 42a/42b.

Step 4. 100 mV is then applied to electrode pair 32a and 32b, and the current is calculated from the voltage measured across resistor 36 and is recorded.

Step 5. Steps 2 to 4 are repeated twice.

Step 6. Lines 52d, 52e and 52f are then opened and the main unit is flushed with DI water.

Step 7. The current recorded in Step 4 is used in comparison to calibration data derived from testing the system with known amounts of total chlorine (see, e.g., Example 2, below) to calculate a level of total chlorine in the water under test. This result can be displayed on a display device (e.g., display device tablet 112 of a dialysis machine 100 or display device 62 of water purification machine 50), and/or an indicator (such as an audible alarm and/or a visual alarm) can be used to notify a user when the amount of total chlorine in the water under test is above (or below) a predetermined threshold (e.g., 0.1 ppm).

As discussed herein, water purification machine 50 can house or operate with the chlorine sensing system 10 of the present disclosure. To that end, chlorine sensing system 10 may be in fluid connection with water purification machine 50 at any suitable location along the fluid path of the machine. Referring now generally to FIGS. 7 to 10, in one embodiment, a water purification machine 50 is in fluid connection with a water source 310. Water source 310 may be any water source suitable for home use including, for example, a municipal water source or a well water source. In the illustrated embodiment, water purification machine 50 includes a water pretreatment filter 320, which may include any number of filters and/or sorbents for removing impurities from the water obtained from the water source 310. In some embodiments, the water pretreatment filter 320 includes a carbon filter. In the embodiment shown in FIG. 7, water pretreatment filter 320 is in fluid connection with chlorine sensing system 10 as described herein. In this embodiment, chlorine sensing system 10 is also in fluid connection with a reverse osmosis filter 330. Reverse osmosis filter 330 is in turn in fluid connection with a drain 370 and an electrodeionization ("EDI") module 340, which in turn may optionally further include an electrodialysis component. The EDI module 340 is in fluid connection with an ultraviolet lamp or filter 350, which in turn is in fluid connection with a bacterial filter 360. Bacterial filter 360 may optionally further include an endotoxin filter. Water treated by water purification machine 50 may be used with a downstream dialysis machine 100, such as a hemodialysis system or home hemodialysis machine as has been described herein.

Figure 8:
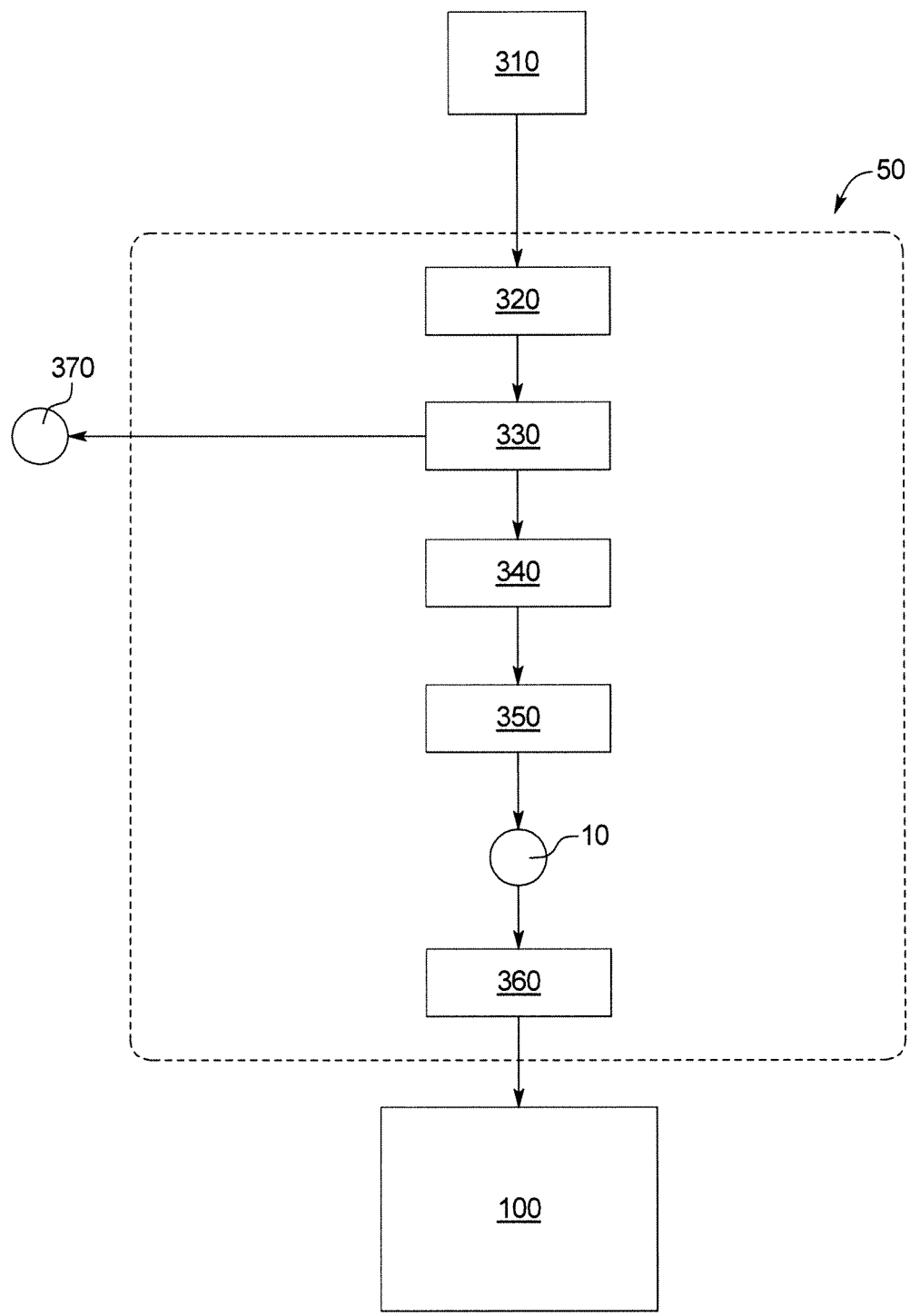
FIG. 8 is a schematic view of one embodiment of a water treatment system which includes a detection cell of the present disclosure.
Figure 9:
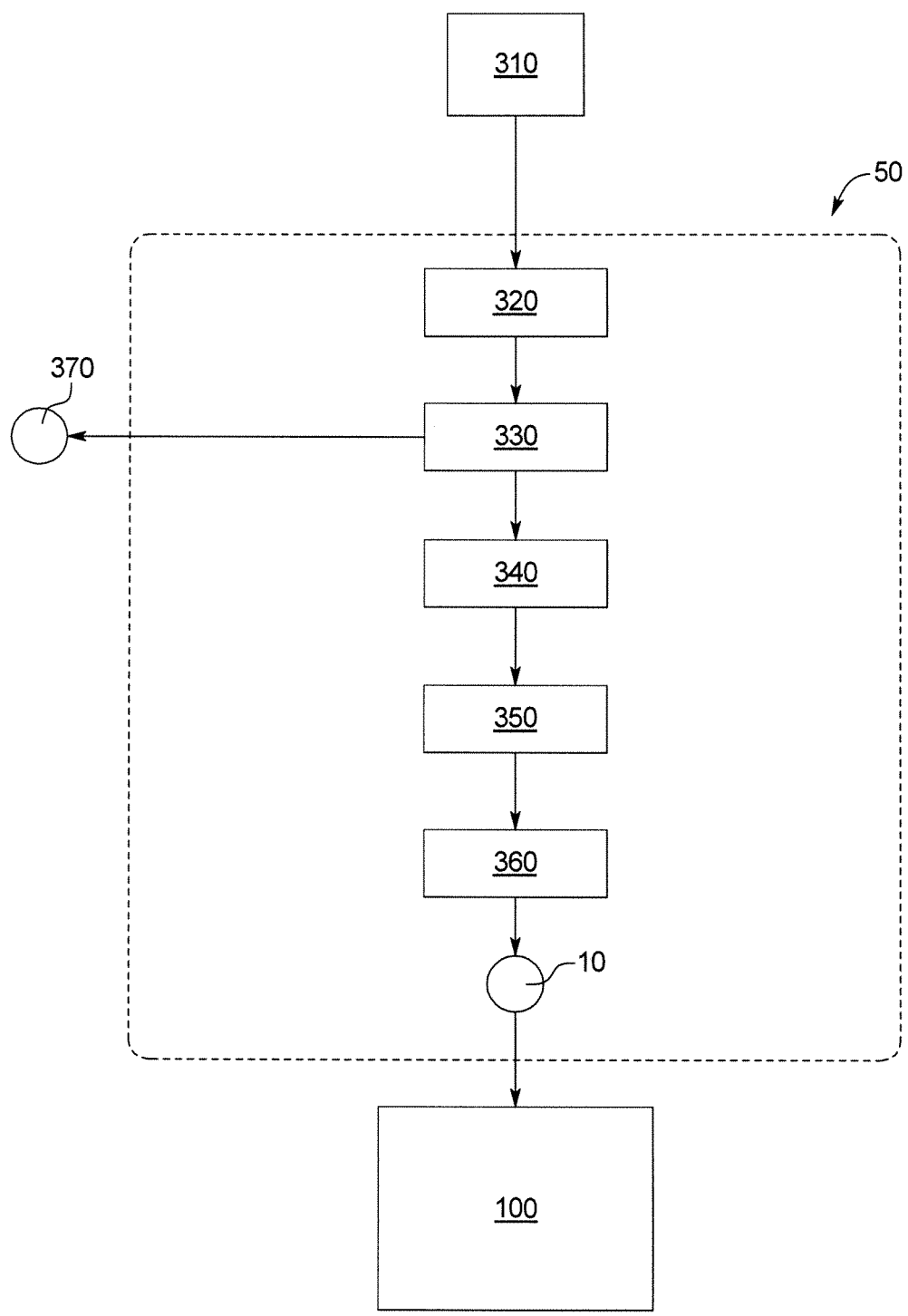
FIG. 9 is a schematic view of one embodiment of a water treatment system which includes a detection cell of the present disclosure.
Figure 10:
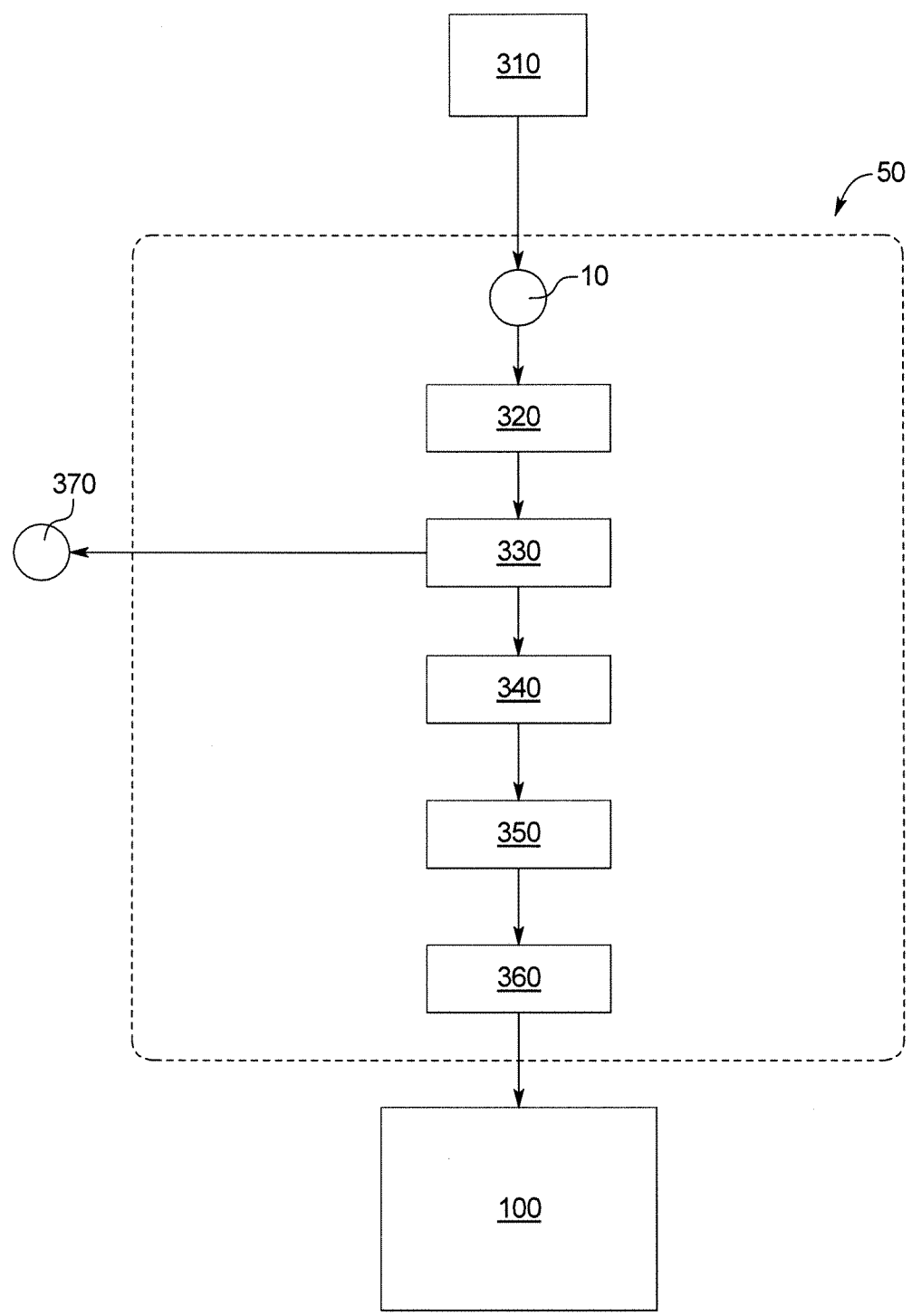
FIG. 10 is a schematic view of one embodiment of a water treatment system which includes a detection cell of the present disclosure.

As illustrated in FIGS. 8 to 10, chlorine sensing system 10 may alternatively be in fluid connection with the ultraviolet lamp or filter 350 and the bacterial filter 360 (FIG. 8); with the bacterial filter 360 and dialysis machine 100 (FIG. 9); or with the water source 310 and the water pretreatment filter 320 (FIG. 10). In some embodiments, the chlorine sensing system 10 is in fluid connection with the water pathway of the water purification machine 50 via a sampling port (not shown).

Aspects of the Present Disclosure

Aspects of the subject matter described herein may be useful alone or in combination with one or more other aspect described herein. Without limiting the foregoing description, in a first aspect of the present disclosure, a dialysis system includes (i) a water purification machine producing an at least partially purified water sample, (ii) a dialysis machine for providing dialysis therapy to a patient, the dialysis machine receiving purified water from the water purification machine, and (iii) a chlorine detection component for determining a level of total chlorine in the at least partially purified water sample, wherein the chlorine detection component includes (a) an iodide reservoir, (b) a reducing agent reservoir, (c) a first chamber in fluid communication with the iodide reservoir and the water purification machine, (d) a second chamber in fluid communication with the reducing agent reservoir, wherein the first and second chambers are separated by a membrane that allows charge but not fluid to pass between the chambers, (e) a first electrode pair associated with a first voltage source, wherein one electrode of the first electrode pair is in contact with iodide fluid and the at least partially purified water sample mixed in the first chamber and the other electrode of the first electrode pair is in contact with a reducing agent solution in the second chamber, and (f) a second electrode pair associated with a second voltage source, wherein both electrodes of the second electrode pair are in contact with the iodide fluid and the at least partially purified water sample mixed in the first chamber.

In accordance with a second aspect of the present disclosure, which can be used in combination with any other aspect or aspects listed herein, at least one of the electrodes includes carbon and/or a conductive metal such as platinum, gold, stainless steel, copper, combinations or alloys thereof.

In accordance with a third aspect of the present disclosure, which can be used in combination with any other aspect or aspects listed herein, at least one of the first and second chambers includes a tube.

In accordance with a fourth aspect of the present disclosure, which can be used in combination with any other aspect or aspects listed herein, the first and second chambers both include tubes, and wherein the first chamber is disposed within a lumen of the second tube.

In accordance with a fifth aspect of the present disclosure, which can be used in combination with any other aspect or aspects listed herein, the membrane is selected from the group consisting of: a semipermeable membrane, and a membrane including a plurality of perforations.

In accordance with a sixth aspect of the present disclosure, which can be used in combination with any other aspect or aspects listed herein, each electrode of the first electrode pair includes or is provided with a resistor.

In accordance with a seventh aspect of the present disclosure, which can be used in combination with any other aspect or aspects listed herein, at least one electrode of the second electrode pair includes or is provided with a resistor.

In accordance with a eighth aspect of the present disclosure, which can be used in combination with any other aspect or aspects listed herein, the dialysis system includes an agitator in contact with at least one of the first and second chambers.

In accordance with a ninth aspect of the present disclosure, which can be used in combination with any other aspect or aspects listed herein, the dialysis system includes a control unit configured and arranged to determine an amount of total chlorine in the at least partially purified water sample via a signal obtained from the second electrode pair.

In accordance with a tenth aspect of the present disclosure, which can be used in combination with any other aspect or aspects listed herein, the chlorine detection component is incorporated within the water purification machine and enables at least one filter of the water purification machine to be evaluated.

In accordance with an eleventh aspect of the present disclosure, which can be used in combination with any other aspect or aspects listed herein, the dialysis system includes a user interface configured and arranged to indicate at least one of (i) an alarm to a user if a level of total chlorine in the at least partially purified water sample exceeds a predetermined value or (ii) indicate a safe status to a user if the level of total chlorine in the at least partially purified water sample falls below a predetermined value.

In accordance with a twelfth aspect of the present disclosure, which can be used with the eleventh aspect in combination with other aspect or aspects listed herein, the predetermined maximum acceptable total chlorine value is between and including 0.1 ppm to 0.5 ppm.

In accordance with a thirteenth aspect of the present disclosure, which can be used in combination with any other aspect or aspects listed herein, at least one of the first chamber, the iodide reservoir, or the reducing agent reservoir is provided in a replaceable cartridge or cassette form.

In accordance with a fourteenth aspect of the present disclosure, which can be used in combination with any other aspect or aspects listed herein, the dialysis system includes a plurality of pumps and valves positioned and arranged to meter preset amounts of the at least partially purified water sample and the iodide into the first chamber and the reducing agent into the second chamber.

In accordance with a fifteenth aspect of the present disclosure, which can be used in combination with any other aspect or aspects listed herein, the dialysis system includes at least one pump and valve positioned and arranged to pump deionized water into at least one of the first and second chambers.

In accordance with a sixteenth aspect of the present disclosure, which can be used in combination with any other aspect or aspects listed herein, the dialysis system includes at least one pump and valve positioned and arranged to pull fluid from at least one of the first and second chambers to drain.

In accordance with a seventeenth aspect of the present disclosure, which can be used in combination with any other aspect or aspects listed herein, the dialysis system prepares dialysate using the water from the water purification machine, and wherein information concerning the level total chlorine is displayed on a user interface of the dialysis machine.

In accordance with a eighteenth aspect of the present disclosure, which can be used in combination with any other aspect or aspects listed herein, the iodide includes potassium iodide.

In accordance with a nineteenth aspect of the present disclosure, which can be used in combination with any other aspect or aspects listed herein, the reducing agent includes sodium sulfate.

In accordance with a twentieth aspect of the present disclosure, which can be used in combination with any other aspect or aspects listed herein, a method of providing hemodialysis to a subject in need thereof includes (i) providing a dialysis system as disclosed herein, wherein the at least partially purified water sample is obtained from water for preparing dialysate, (ii) determining a level of total chlorine in the at least partially purified water sample, (iii) alerting the user to take a corrective action if the level of total chlorine exceeds a predetermined level, and (iv) allowing the user to perform the hemodialysis treatment if the level of total chlorine is below the predetermined level.

In accordance with a twenty-first aspect of the present disclosure, which can be used with the twentieth aspect in combination with any other aspect or aspects listed herein, the alerting step further includes preventing the user from performing the hemodialysis treatment until a subsequent level of total chlorine in a subsequent at least partially purified water sample is below the predetermined level.

In accordance with a twenty-second aspect of the present disclosure, which can be used in combination with any other aspect or aspects listed herein, a method of determining an amount of total chlorine in an at least partially purified water sample associated with renal failure therapy includes (i) providing a water purification machine, (ii) providing a dialysis machine, said dialysis machine receiving purified water from the water purification machine, and (iii) providing a total chlorine detection system in fluid communication with the water purification machine and the dialysis machine, wherein the total chloride detection system includes (a) a first electrode pair configured to generate tri-iodide in the presence of iodide and a total chlorine compound upon application of a first voltage, and (b) a second electrode pair in fluid communication with the first electrode pair, the second electrode pair configured to determine a current associated with the tri-iodide generated by the first electrode pair upon application of a second voltage to the second electrode pair, (iv) providing an at least partially purified water sample, the at least partially purified water sample including an amount of total chlorine, (v) monitoring a background current via a tri-iodide detection circuitry, the background current associated with an amount of tri-iodide present in the system before introduction of a water sample, (vi) metering an amount of the at least partially purified water sample into the total chlorine detection system, (vii) monitoring a baseline current via a tri-iodide detection circuitry, the baseline current associated with the amount of total chlorine in the at least partially purified water sample, (viii) generating a first amount of tri-iodide from the at least partially purified water sample by application of a first voltage to the first electrode pair, (ix) monitoring a first current by application of a second voltage to the second electrode pair, the first current associated with the sum of the amount of total chlorine and the first amount of tri-iodide, (x) generating a second amount of tri-iodide from the at least partially purified water sample by application of a third voltage to the first electrode pair, (xi) monitoring a second current by application of a fourth voltage to the second electrode pair, the second current associated with the sum of the amount of total chlorine and the first and second amounts of tri-iodide, (xii) optionally generating a third amount of tri-iodide from the at least partially purified water sample by application of a fifth voltage to the first electrode pair, (xiii) optionally monitoring a third current induced by application of a sixth voltage to the second electrode pair, the third current associated with the sum of the amount of total chlorine and the first, second and third amounts of tri-iodide, and (xiv) calculating the amount of total chlorine in the at least partially purified water sample using the baseline current, the background current, and at least one of the first current, the second current, and the optional third current.

In accordance with a twenty-third aspect of the present disclosure, which can be used in combination with any other aspect or aspects listed herein, a plurality of subsequent or sequential voltages applied to the tri-iodide generating circuit are the same or substantially the same.

In accordance with a twenty-fourth aspect of the present disclosure, which can be used in combination with any other aspect or aspects listed herein, a plurality of subsequent or sequential voltages applied to the tri-iodide detecting circuit are the same or substantially the same.

In accordance with a twenty-fifth aspect of the present disclosure, which can be used in combination with any other aspect or aspects listed herein, a method of determining an amount of total chlorine in an at least partially purified water sample associated with renal failure therapy includes (i) providing an at least partially purified water sample from a water purification machine, said water purification machine in fluid communication with a dialysis machine (ii) monitoring a background current in the system, the background current associated with the amount of any tri-iodide present in the system before introduction of the water sample, (iii) metering out an amount of the at least partially purified water sample, (iv) monitoring a baseline current in the at least partially purified water sample by application of a first voltage to the at least partially purified water sample, the baseline current corresponding to the amount of total chlorine in the water sample, (v) generating a first amount of tri-iodide from the at least partially purified water sample, (vi) monitoring a first current associated with the sum of the total chlorine and the first amount of tri-iodide, (vii) generating a second amount of tri-iodide from the at least partially purified water sample, (viii) monitoring a second current associated with the sum of the total chlorine and the first and second amounts of tri-iodide, (ix) optionally generating a third amount of tri-iodide from the at least partially purified water sample, (x) optionally monitoring a third current associated with the sum of the amount of total chlorine and the first, second and optional third amounts of tri-iodide, and (xi) calculating the total chlorine concentration in the at least partially purified water sample using the background current, the baseline current and at least two of the first current, the second current, and the third current.

In accordance with a twenty-fourth aspect of the present disclosure, any of the structure and functionality illustrated or described in connection with FIGS. 1 to 10 can be used in combination with other aspect or aspects listed herein.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A dialysis system comprising:
a water purification machine producing an at least partially purified water sample;
a dialysis machine for providing dialysis therapy to a patient, the dialysis machine receiving purified water from the water purification machine; and
a chlorine detection component for determining a level of total chlorine in the at least partially purified water sample, wherein the chlorine detection component includes:
an iodide reservoir configured to store iodide fluid,
a reducing agent reservoir configured to store a reducing agent,
a first chamber in fluid communication with the iodide reservoir and the water purification machine,
a second chamber in fluid communication with the reducing agent reservoir, wherein the first and second chambers are separated by a membrane that allows an electrical charge but not fluid to pass between the chambers,
a first electrode pair associated with a first voltage source, wherein one electrode of the first electrode pair is in electrical contact with an interior of the first chamber and the other electrode of the first electrode pair is in electrical contact with an interior of the second chamber, and
a second electrode pair associated with a second voltage source, wherein both electrodes of the second electrode pair are in electrical contact with an interior of the first chamber.

2. The system of claim 1, wherein at least one of the electrodes includes carbon and/or a conductive metal.

3. The system of claim 1, wherein at least one of the first and second chambers includes a tube.

4. The system of claim 1, wherein the first and second chambers both include tubes, and wherein the first chamber is disposed within a lumen of the second tube.

5. The system of claim 1, wherein the membrane is a semipermeable membrane.

6. The system of claim 1, wherein each electrode of the first electrode pair includes or is provided with a resistor.

7. The system of claim 1, wherein at least one electrode of the second electrode pair includes or is provided with a resistor.

8. The system of claim 1, which includes an agitator, baffle, stirrer, or vibration mechanism in contact with at least one of the first and second chambers to mix fluid in the first and/or second chamber.

9. The system of claim 1, which includes a control unit configured and arranged to determine an amount of total chlorine in the at least partially purified water sample via a signal obtained from the second electrode pair.

10. The system of claim 1, wherein the chlorine detection component is incorporated within the water purification machine and enables at least one filter of the water purification machine to be evaluated.

11. The system of claim 1, which includes a user interface configured and arranged to indicate at least one of (i) an alarm to a user if a level of total chlorine in the at least partially purified water sample exceeds a predetermined value or (ii) a safe status to a user if the level of total chlorine in the at least partially purified water sample falls below a predetermined value.

12. The system of claim 11, wherein the predetermined value is a value within a range between and including 0.01 ppm to 0.5 ppm.

13. The system of claim 1, wherein at least one of the first chamber, the iodide reservoir, or the reducing agent reservoir is provided in a replaceable cartridge or cassette form.

14. The system of claim 1, which includes a plurality of pumps and valves positioned and arranged to meter preset amounts of the at least partially purified water sample and the iodide into the first chamber and the reducing agent into the second chamber.

15. The system of claim 1, which includes at least one pump and valve positioned and arranged to pump deionized water into at least one of the first and second chambers.

16. The system of claim 1, which includes at least one pump and valve positioned and arranged to pull fluid from at least one of the first and second chambers to drain.

17. The system of claim 1, which prepares dialysate using the water from the water purification machine, and wherein information concerning the level total chlorine is displayed on a user interface of the dialysis machine.

18. The system of claim 2, wherein the conductive metal includes at least one of platinum, gold, stainless steel, copper, and combinations or alloys thereof.

19. The system of claim 5, wherein the membrane includes a plurality of perforations.

* * * * *